US007432409B2

(12) United States Patent
Elomari et al.

(10) Patent No.: US 7,432,409 B2
(45) Date of Patent: *Oct. 7, 2008

(54) ALKYLATION PROCESS USING CHLOROALUMINATE IONIC LIQUID CATALYSTS

(75) Inventors: Saleh Elomari, Fairfield, CA (US); Steve Trumbull, San Leandro, CA (US); Hye Kyung C. Timken, Albany, CA (US); Robert Cleverdon, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 11/021,165

(22) Filed: Dec. 21, 2004

(65) Prior Publication Data

US 2006/0135839 A1 Jun. 22, 2006

(51) Int. Cl.
*C07C 2/54* (2006.01)
(52) U.S. Cl. .................. 585/722; 585/727; 585/728
(58) Field of Classification Search .......... 585/722, 585/727, 728
See application file for complete search history.

(56) References Cited

U.S. PATENT DOCUMENTS

| | | | |
|---|---|---|---|
| 3,764,637 A * | 10/1973 | Lyon | 585/721 |
| 4,764,440 A | 8/1988 | Jones et al. | |
| 5,510,561 A | 4/1996 | Sherman et al. | |
| 5,593,569 A | 1/1997 | Sherman | |
| 5,654,251 A | 8/1997 | Abbott et al. | |
| 5,693,585 A | 12/1997 | Benazzi et al. | |
| 5,731,101 A | 3/1998 | Sherif et al. | |
| 5,750,455 A | 5/1998 | Chauvin et al. | |
| 5,824,832 A | 10/1998 | Sherif et al. | |
| 5,827,602 A | 10/1998 | Koch et al. | |
| 6,028,024 A | 2/2000 | Hirschauer et al. | |
| 6,235,959 B1 | 5/2001 | Hirschauer et al. | |
| 6,288,281 B1 | 9/2001 | Nemeth et al. | |
| 6,797,853 B2 | 9/2004 | Houzvicka et al. | |
| 2003/0060359 A1 | 3/2003 | Olivier-Bourbigou et al. | |
| 2004/0077914 A1 | 4/2004 | Zavilla et al. | |
| 2004/0133056 A1 | 7/2004 | Liu et al. | |

OTHER PUBLICATIONS

Gale, et al. Potentiometric Investigation of Dialuminum Heptachloride Formation in Aluminum Chloride-1-Butylpyridinium Choloride Mixtures, National Technical Information Service, Oct. 18, 1978, 1603-1605, Contribution from the Department of Chemistry, Colorado State University, Fort Collins, Colorado 80523 USA.
Gilbert, et al. Raman Spectra of Molten Aluminum Chloride: 1-Butylpyridinium Chloride Systems at Ambient Temperatures; Inorganic Chemistry, vol. 17. No. 10, 1978, pp. 2728-2729; contribution from the Department of Chemistry, Colorado State University, Fort Collins, Colorado 80523 USA.

Robinson, et al. 1H and 13C Nuclear Magnetic Resonance Spectroscopy Studies of Aluminum Halide-Alkylpyridinium Halide Molten Salts and Their Benzene Solutions; Jul. 4, 1979, Journal of the American Chemical Soscienty 101:14 pp. 3776-3779. Contribution from the Department of Chemistry, Colorado State University, Fort Collins, Colorado USA.
Gale, et al. Infrared Spectral Investigations of Room-Temperature Aluminum Chloride-1-Butylpyridinium Chloride Melts; 1980 American Chemical Society, Oct. 19, 1979, pp. 2240-2242. Contribution from the Department of Chemistry, Colorado State University, Fort Collins Colorado USA.
Lipztajn, et al. On Ionic Association in Ambient Temperature Chloroaluminate Molten Salts. Analysis of Electrochemical and Conductance Data. J. Electrochem. Soc: Electrochemical Science and Technology May 1985 vol. 132, No. 5 pp. 1126-1130. Department of Chemistry, State University of New York at Buffalo, New York USA.
Bertlein, et al. Stabilisierung von Carbenium-Ionen durch Acide Salzschmelzen—eine NMR-Studie, Eingegangen am 2. Marz 1989. Chem. Ber. 122 (1989) 1661-1663. Institut fur Physikalische und Theoretische Chemie der Universitat Erlangen-Nurnberg, EgerlandstraBe 3, D-8520 Erlangen Germany.
Okoturo, et al. Temperature Dependence of Viscosity for Room Temperature Ionic Liquids. Journal of Electroanalytical Chemistry 568 (2004) 167-181 2004 Elsevier B.V. Chemistry Department, Queen Mary, University of London, Mile End Road, London E1 3NS, UK.
Yoo, et al. Ionic Liquid-Catalyzed Alkylation of Isobutane with 2-Butene. Journal of Catalysis 222 (2004) 511-519. 2004 Elsevier, Inc. Department of Chemical and Material Engineering, University of Cincinnati, Cincinnati, Ohio USA, Clean Processes Branch, National Risk Management Research Lab, US Environmental Protection Agency, MS 443, Cincinnati, Ohio USA.

* cited by examiner

*Primary Examiner*—Thuan Dinh Dang
(74) *Attorney, Agent, or Firm*—Susan M. Abernathy; Steven H. Roth

(57) ABSTRACT

A process for the production of a high quality gasoline blending components from refinery process streams by the alkylation of light isoparaffins with olefins using an ionic liquid catalyst is disclosed. The process includes reacting a refinery stream containing isopentane and/or isobutane with a refinery stream containing ethylene and/or propylene and butylenes under alkylation conditions in the presence of a chloroaluminate ionic liquid catalyst comprising a hydrocarbyl substituted pyridinium chloroaluminate or a hydrocarbyl substituted imidazolium chloroaluminate of the general formulas A and B, respectively.

A

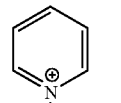

B

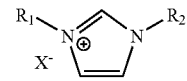

Where R═H, methlyl, ethyl, propyl, butyl, pentyl or hexyl group and X is a chloroaluminate, and R1 and R2═H, methyl, ethyl, propyl, butyl, pentyl or hexyl group and where R1 and R2 may or may not be the same.

36 Claims, 1 Drawing Sheet

Continuous Alkylation of Isopentane and Ethylene
Effect of HCl Co-Catalyst on Catalyst Deactivation

ALKYLATION PROCESS USING CHLOROALUMINATE IONIC LIQUID CATALYSTS

FIELD OF THE INVENTION

The present invention relates to a process for the production of a high quality gasoline blending components from refinery process streams by the alkylation of light isoparaffins with olefins using an ionic liquid catalyst.

BACKGROUND OF THE INVENTION

In general, conversion of light paraffins and light olefins to more valuable cuts is very lucrative to the refining industries. This has been accomplished by alkylation of paraffins with olefins, and by polymerization of olefins. One of the most widely used processes in this field is the alkylation of isobutane with $C_3$ to $C_5$ olefins to make gasoline cuts with high octane number using sulfuric and hydrofluoric acids. This process has been used by refining industries since the 1940's. The process was driven by the increasing demand for high quality and clean burning high-octane gasoline.

Alkylate gasoline is a high quality and efficient burning gasoline that constitutes about 14% of the gasoline pool. Alkylate gasoline is typically produced by alkylating refineries isobutane with low-end olefins (mainly butenes). Currently, alkylates are produced by using HF and $H_2SO_4$ as catalysts. Although these catalysts have been successfully used to economically produce the best quality alkylates, the need for safer and environmentally friendlier catalysts systems has become an issue to the industries involved.

The quest for an alternative catalytic system to replace the current environmentally unfriendly catalysts has been the subject of varying research groups in both academic and industrial institutions. Unfortunately, thus far, no viable replacement to the current processes has been put into practice at commercial refineries.

In the last decade or so, the emergence of chloroaluminate ionic liquids sparked some interest in $AlCl_3$-catalyzed alkylation in ionic liquids as a possible alternative. For example, the alkylation of isobutane with butenes and ethylene in ionic liquids has been described in U.S. Pat. Nos. 5,750,455; 6,028,024; and 6,235,959 and open literature (*Journal of Molecular Catalysis*, 92 (1994), 155-165; "*Ionic Liquids in Synthesis*", P. Wasserscheid and T. Welton (eds.), Wiley-VCH Verlag, 2003, pp 275).

Consider too that modern refineries employ many upgrading units such as fluidic catalytic cracking (FCC), hydrocracking (HCR), alkylation, and paraffin isomerization. As a result, these refineries produce a significant amount of isopentane. Historically, isopentane was a desirable blending component for gasoline having a high octane (92 RON), although it exhibited high volatility (20.4 Reid vapor pressure, RVP). As environmental laws began to place more stringent restrictions on gasoline volatility, the use of isopentane in gasoline was limited because of its high volatility. As a consequence, the problem of finding uses for by-product isopentane became serious, especially during the hot summer season. Moreover, as more gasoline compositions contain ethanol instead of MTBE as their oxygenate component, more isopentane must be kept out of the gasoline pool in order to meet the gasoline volatility specification. So, the gasoline volatility issue becomes even more serious, further limiting the usefulness of isopentane as a gasoline blending component.

Heretofore, refiners have not used ethylene-containing streams for the alkylation of isopentane because the reaction is not catalyzed by the conventional acid alkylation catalysts. Using an ionic liquid catalyst allows refiners to enjoy the above described benefits.

SUMMARY OF THE INVENTION

The present invention relates to a process for the production of high quality gasoline blending components comprising reacting a refinery stream containing isopentane and/or isobutane with a refinery stream containing ethylene and/or propylene and butylenes under alkylation conditions in the presence of a chloroaluminate ionic liquid catalyst comprising a hydrocarbyl substituted pyridinium choroaluminate or a hydrocarbyl substituted imidazolium chloroaluminate of the general formulas A and B, respectively.

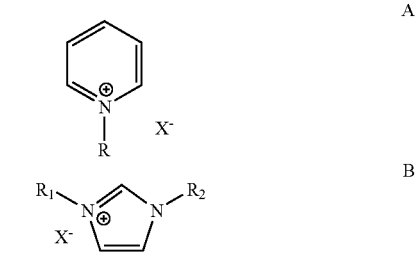

Where R=H, methyl, ethyl, propyl, butyl, pentyl or hexyl group and X is a chloroaluminate, and $R_1$ and $R_2$=H, methyl, ethyl, propyl, butyl, pentyl or hexyl group and where $R_1$ and $R_2$ may or may not be the same.

DETAILED DESCRIPTION

Figure 1:
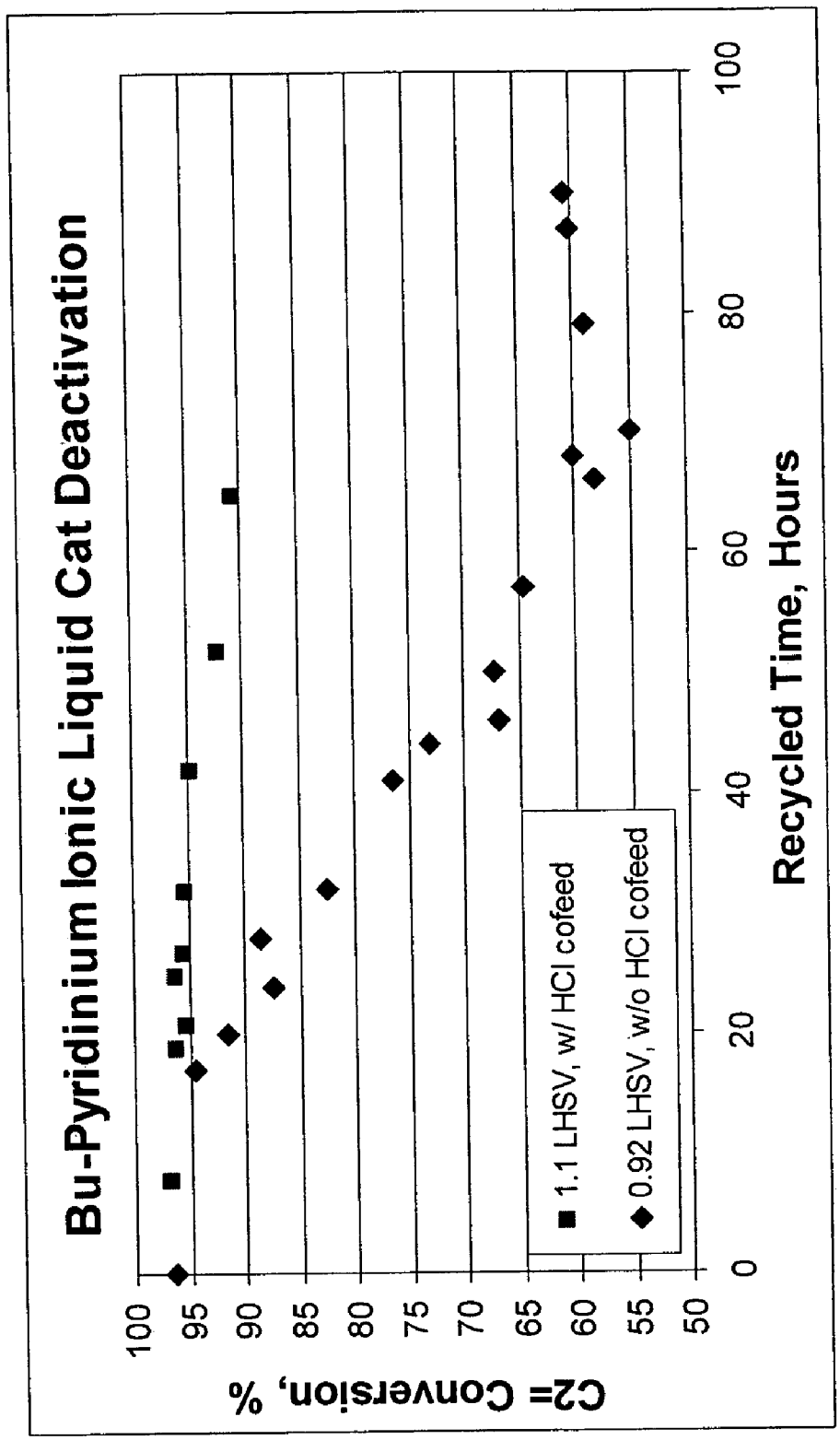
FIG. 1 is a plot of ethylene conversion monitored in the continuous mode while recycling the catalyst.

The present invention is based in part on our investigation of the alkylation of isobutane and isopentane with ethylene catalyzed by aluminum chloride in ionic liquids and on our surprising discovery that the course of the alkylation reaction and in particular the conversion of ethylene is greatly and unexpectedly influenced by the kind of ionic liquid used in the alkylation reactions. Our investigation of the alkylation showed that pyridinium and imidazolium-based chloroaluminate ionic liquids are surprisingly much more effective in the alkylation of isopentane and isobutane with ethylene than aliphatic ammonium chloroaluminate ionic liquids (such as tributyl-methyl-ammonium chloroaluminate). We have shown, for example, that 1-butyl-3-methyl-imidazolium chloroaluminate and 1-butyl-pyridinium chloroaluminate results in greater than 95% ethylene conversion while tr-butyl-methyl-ammonium chloroaluminate results only in low-to-fair ethylene conversion during the alkylation of isobutane and isopentane with ethylene gas.

Improving the alkylation rate of $AlCl_3$-catalyzed alkylation of ethylene with light iso-paraffins by increasing the rate of ethylene conversion was due to using pyridinium and imidazolium based ionic liquids. These ionic liquids are superior to aliphatic ionic liquids and tremendously increase the conversion rate of ethylene. Complete and near complete conversions of ethylene were observed in these ionic liquids, while low to moderate conversions were observed in the aliphatic counterparts.

In one embodiment, the present invention provides a process for the production of high quality gasoline blending components comprising reacting a refinery stream containing isopentane with a refinery stream containing ethylene, which may also contain propylene, butylenes and/or pentenes under alkylation conditions in the presence of a chloroaluminate ionic liquid catalyst comprising a hydrocarbyl substituted pyridinium halide or a hydrocarbyl substituted imidazolium halide.

The ionic liquid catalyst is preferably selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

The ionic liquid catalyst, which is the most preferred for the process of the present invention, is N-butylpyridinium chloroaluminate ($C_5H_5NC_4H_9Al_2Cl_7$).

A metal halide may be employed to modify the catalyst activity and selectivity. The metal halides most commonly used as inhibitors/modifiers in aluminum chloride-catalyzed olefin-isoparaffin alkylations include NaCl, LiCl, KCl, $BeCl_2$, $CaCl_2$, $BaCl_2$, $SrCl_2$, $MgCl_2$, $PbCl_2$, $CuCl$, $ZrCl_4$ and AgCl, as described by Roebuck and Evering (Ind. Eng. Chem. Prod. Res. Develop., Vol. 9, 77, 1970). Preferred metal halides are CuCl, AgCl, $PbCl_2$, LiCl, and $ZrCl_4$.

HCl or any Broensted acid may be employed as co-catalyst to enhance the activity of the catalyst by boasting the overall acidity of the ionic liquid-based catalyst. The use of such co-catalysts and ionic liquid catalysts that are useful in practicing the present invention is disclosed in U.S. Published Patent Application Nos. 2003/0060359 and 2004/0077914. Other co-catalysts that may be used to enhance the activity include IVB metal compounds preferably IVB metal halides such as $ZrCl_4$, $ZrBr_4$, $TiCl_4$, $TiCl_3$, $TiBr_4$, $TiBr_3$, $HfCl_4$, $HfBr_4$ as described by Hirschauer et al. in U.S. Pat. No. 6,028,024.

In a process according to the present invention, the refinery stream containing ethylene, which may also contain other light olefins such as propylene, butylenes and pentenes, may be derived by providing a first ethylene-containing refinery stream and separating a $C_{2+}$ fraction from said first stream to produce said refinery stream containing ethylene, which is richer in ethylene than said first ethylene-containing refinery stream.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1 to 100, for example, advantageously in the range 2 to 50, preferably in the range 2 to 20. In a semi-batch system the isoparaffin is introduced first then the olefin, or a mixture of isoparaffin and olefin. Catalyst volume in the reactor is in the range of 2 vol % to 70 vol %, preferably in the range of 5 vol % to 50 vol %. Vigorous stirring is desirable to ensure good contact between the reactants and the catalyst. The reaction temperature can be in the range −40° C. to +150° C., preferably in the range −20° C. to +100° C. The pressure can be in the range from atmospheric pressure to 8000 kPa, preferably sufficient to keep the reactants in the liquid phase. Residence time of reactants in the vessel is in the range a few seconds to hours, preferably 0.5 min to 60 min. The heat generated by the reaction can be eliminated using any of the means known to the skilled person. At the reactor outlet, the hydrocarbon phase is separated from the ionic phase by decanting, then the hydrocarbons are separated by distillation and the starting isoparaffin which has not been converted is recycled to the reactor.

Typical reaction conditions may include a catalyst volume in the reactor of from 5 vol % to 50 vol %, a temperature of from −10° C. to +100° C., a pressure of from 300 kPa to 2500 kPa, an isopentane to olefin molar ratio of from 2 to 8 and a residence time of 5 min to 1 hour.

In a process according to the present invention, high quality gasoline blending components of low volatility are recovered from said alkylation zone. Those blending components are then preferably blended into gasoline.

The following Examples are illustrative of the present invention, but are not intended to limit the invention in any way beyond what is contained in the claims which follow.

EXAMPLES

Chloroaluminate ionic liquids have been used in a variety of catalytic reactions and processes. However, not much attention has been devoted to the role of the cationic portion of the ionic liquid (namely the quaternary ammonium cation) in most of the reported catalytic processes. As further described herein, we investigated the alkylation of ethylene with isobutane and isopentane in four different ionic liquids and found the course of the reaction, especially the conversion of ethylene (the limiting reagent), to be highly influenced by the type of ionic liquid used in the process. For example, good conversion to complete conversion of ethylene was achieved in 1-butyl-4-methyl pyridinium chloroaluminate, 1-butyl pyridinium chloroaluminate and 1-butyl-3-methyl imidazolium chloroaluminate. However, only poor to moderate conversions were obtained in tri-butyl-methyl ammonium chloroaluminate. Such rate increase reduces the residence time of the reaction and hence reduces the many possible undesired side reactions during the alkylation. Consequently, an alkylation process in accordance with the present invention results in higher selectivity and higher alkylates quality.

Example 1

The Preparation of N-Butyl-Pyridinium Chloroaluminate Ionic Liquid

N-butyl-pyridinium chloroaluminate is a room temperature ionic liquid prepared by mixing neat N-butyl-pyridinium chloride (a solid) with neat solid aluminum trichloride in an inert atmosphere. The syntheses of butylpyridinium chloride and the corresponding N-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 145° C. under autogenic pressure over night. Then, the autoclave was cooled down to room temperature, vented and the resultant mixture was transferred to a three liter round bottom flask. Chloroform was used to rinse the liner and dissolve the stubborn crusty product that adhered to the sides of the liner. Once all transferred, the mixture was concentrated at reduced pressure on a rotary evaporator (in a hot water bath) to remove excess chloride, un-reacted pyridine and the chloroform rinse. The obtained tan solid product was further purified by dissolving in hot acetone and precipitating the pure product through cooling and addition of diethyl ether. Filtering and drying under vacuum and heat on a rotary evaporator gave 750 gm (88% yields) of the desired product as an off-white shinny solid. 1H-NMR and 13C-NMR were ideal for the desired N-butyl-pyridinium chloride and no presence of impurities was observed by NMR analysis.

N-butylpyridinium chloroaluminate was prepared by slowly mixing dried N-butylpyridinium chloride and anhydrous aluminum chloride ($AlCl_3$) according to the following procedure. The N-butylpyridinium chloride (prepared as described above) was dried under vacuum at 80° C. for 48 hours to get rid of residual water (N-butylpyridinium chloride is hydroscopic and readily absorbs water from exposure to air). Five hundred grams (2.91 mol.) of the dried N-butylpyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the $AlCl_3$ was added, the resulting amber-looking liquid was left to gently stir overnight in the glove box. The liquid was then filtered to remove any un-dissolved $AlCl_3$. The resulting acidic N-butyl-pyridinium chloroaluminate was used as the catalyst for the alkylation of isopentane with ethylene.

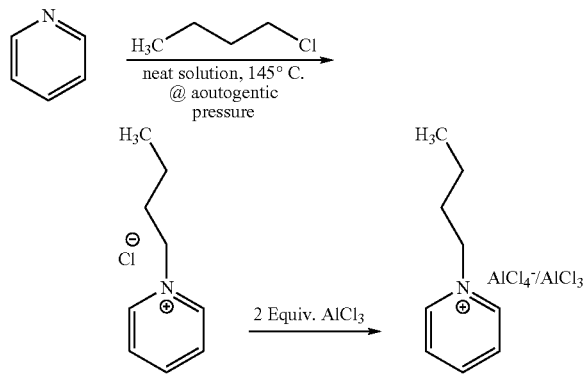

Example 2

Alkylation of Isopentane with Ethylene in Different Ionic Liquids

The cation portion (the organic portion) of the ionic liquid plays a very important role in the chemical process taking place in ionic liquids. The nature of the ammonium cation (organic portion) plays a crucial role in determining many of the chemical and physical properties of the ionic liquid system such as polarity, viscosity, solution, solvation, stabilization of intermediates and other properties. To study the effect of the ionic liquid type on the alkylation chemistry of isoparaffins with olefins, we investigated the alkylation of isopentane with ethylene in five different ionic liquids under identical reaction conditions. These ionic liquids are shown below and are:

1-butyl-4-methyl-pyridinium chloroaluminate (BMP), 1-butyl-pyridinium chloroaluminate (BP), 1-butyl-3-methyl-imidazolium chloroal uminate BMIM), 1-H-pyridinium chloroaluminate (HP) and tributyl-methyl-ammonium chloroaluminate (TBMA):

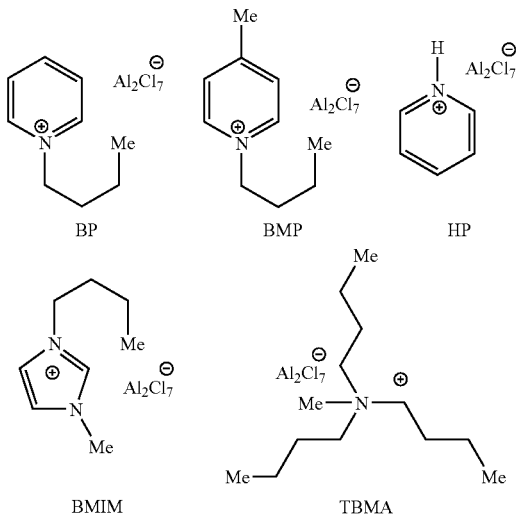

Table 1 below shows the results of alkylating isopentane with ethylene in aforementioned ionic liquids.

TABLE 1

|  | BMP* | BP* | TBMA* | BMIM* | HP |
|---|---|---|---|---|---|
| $iC_5$/ethylene | 3.9 | 3.9 | 3.8 | 3.9 |  |
| Temp. | 50° C. | 50° C. | 50° C. | 50° C. | 50° C. |
| Starting Pressure kPa | 945 | 890 | 869 | 966 | 834 |
| Ending Pressure kPa | 290 | 76 | 538 | 69 | 83 |
| $AlCl_3/iC_5$ | 0.07 | 0.07 | 0.07 | 0.07 | 0.07 |
| $AlCl_3$/ethylene | 0.26 | 0.26 | 0.26 | 0.25 | 0.27 |
| Completion time | 60 min | 27 min | 62 min | 31 min | 26 min |
| Selectivity. % |  |  |  |  |  |
| $C_{3-}$ | 0.72 | 0.00 | 0.60 | 0.00 | 0.13 |
| $C_4$ | 0.94 | 1.16 | 0.49 | 1.17 | 0.94 |
| $C_5$ | 72.71 | 67.73 | 79.70 | 67.09 | 68.81 |
| $C_6$ | 1.03 | 1.40 | 0.55 | 1.37 | 1.54 |
| $C_7$ | 17.95 | 21.88 | 14.02 | 22.67 | 18.95 |
| $C_8$ | 2.71 | 3.40 | 1.87 | 3.20 | 3.34 |
| $C_9$ | 2.00 | 1.91 | 1.50 | 2.12 | 2.62 |
| $C_{10}$ | 1.50 | 1.42 | 0.87 | 1.40 | 1.79 |
| $C_{11}$ | 0.35 | 0.67 | 0.30 | 0.61 | 0.83 |
| $C_{12+}$ | 0.08 | 0.43 | 0.09 | 0.38 | 1.06 |
| Ethylene conversion | 65% (±5%) | >97% | ~55% | >97% | >97% |

Table 1 shows differences in the alkylation outcome from one ionic liquid to another. Ethylene conversion reached completion or near completion in pyridinium and in imidazolium-based ionic liquids while reactions in tetra-alkyl-ammonium-based ionic liquids (alkyl amines-based ionic liquids) led only to poor or moderate conversions. The data clearly indicate that aromatic amines-based ionic liquids are much better for isoparaffins/light olefins alkylation than simple alkyl amines-based ionic liquids. Among the pyridinium-based ionic liquid catalysts, 1-butylpyridinum (BP) and 1-H-pyridinium chloroaluminate (HP) showed higher ethylene conversion than 1-butyl-4-methyl-pyridinium (BMP). 1-H-pyridinium chloroaluminate (HP), however, led to the formation of more $C_9+$ products than the other two pyridinium-based catalysts. Both 1-butylpyridium (BP) and 1-butyl-3-methyl-imidazolium (BMP) catalysts showed the best activity and selectivity. Based on the results shown in Table 1, the preferred catalyst for the alkylation is an acidic chloroaluminate ionic liquid catalyst system comprising an alkyl substituted pyridinium halide or an alkyl substituted imidazolium halide.

While not being bound to any theory, these differences may be due to the varying degrees in the ability of each ionic liquid in solvating the reacting species and reaction intermediates. The solubility of hydrocarbons is very minimal in ionic liquids. Consequently, the alkylation of isopentane with ethylene in ionic liquids is biphasic (and perhaps triphasic) system. Hence, the alkylation and other chemical transformations in ionic liquids are interfacial and their progress is greatly influenced by mass transfer and surface area. The more efficient the mass transfer the more effective the chemical exchange between the involved substrates and the catalyst. Therefore, the nature of the organic portion (cation) of the ionic liquid greatly influences the viscosity of the ionic liquid and its solvation power and hence mass transfer during alkylation.

Example 3

Continuous Alkylation of Isopentane with Ethylene with HCl Co-Feeding

Evaluation of ethylene alkylation with isopentane was performed in a 100 cc continuously stirred tank reactor. A 4:1 molar ratio of isopentane and ethylene mixture was fed to the reactor while vigorously stirring at 1600 RPM. An ionic liquid catalyst, N-butylpyridinium chloroaluminate, was fed to the reactor via a second inlet port targeting to occupy 15 vol % in the reactor. A small amount of anhydrous HCl gas was added to the process (10:1 molar ratio of catalyst to HCl). The average residence time for the combined volume of feeds and catalyst was about 40 min. The outlet pressure was maintained at 2300 kPa using a backpressure regulator. The reactor temperature was maintained at 50° C. The reactor effluent was separated in a 3-phase separator into $C_4$— gas; alkylate hydrocarbon phase, and the ionic liquid catalyst. The recovered ionic liquid catalyst was recycled back to the reactor while no new catalyst was added. Performance of the catalyst was monitored for 65 hrs. Summary of operating conditions and yield information are summarized in Table 2 and ethylene conversion as a function of recycle time is plotted in FIG. 1.

Example 4

Continuous Alkylation of Isopentane with Ethylene without HCl Co-Feeding

The effect of HCl co-catalyst was evaluated in another continuous run where no HCl was added to the reactor. Other conditions were similar to those in Example 3. The operating conditions and yield information are summarized in Table 2 and ethylene conversion as a function of recycle time is plotted in FIG. 1.

TABLE 2

Continuous Alkylation of Isopentane and Ethylene

|  | Example 3 | Example 4 |
| --- | --- | --- |
| Temperature, ° C. | 50 | 50 |
| Total Pressure, kPa | 2300 | 2200 |
| Catalyst Vol. Fraction | 0.15 | 0.19 |
| External I/O Ratio, molar | 4.0 | 4.0 |
| Olefin Space Velocity/Vol. of Cat (LHSV) | 1.1 | 0.92 |
| Catalyst to HCl Ratio, molar | 10 | No HCl |
| Residence Time of Reactant, min | 40 | 40 |
| Performance at early on stream | (21 hours-on-stream) | (17 hours-on-stream) |
| Conversion of Ethylene, wt % | 95 | 94 |
| Selectivity of Converted Products, wt % |  |  |
| $C_{4-}$ | 4.3 | 3.1 |
| $nC_5$ + neo $C_5$ | 2.1 | 1.4 |
| $C_6$ | 4.2 | 3.3 |
| $C_7$ | 78.6 | 79.9 |
| $C_8$ | 1.4 | 1.2 |
| $C_9$ | 7.0 | 8.8 |
| $C_{10+}$ | 2.4 | 2.3 |
| Total | 100.0 | 100.0 |

Results in Table 2 indicate that the alkylation process of the present invention is highly selective in that nearly 80% of the converted product is $C_7$ isoparaffins. A comparable initial ethylene conversion was obtained at a higher olefin space velocity with the HCl addition, indicating that addition of HCl increases the catalyst activity. Similar activity increased was observed earlier in batch testing. The HCl addition did not affect the product selectivity in that the overall product selectivity is comparable to the no HCl addition case. FIG. 1 is a plot of ethylene conversion monitored in the continuous mode for up to 90 hours on stream while recycling the catalyst continuously. We were surprised by the effect of HCl in maintaining the ethylene conversion activity. Without HCl addition, the ethylene conversion dropped steadily from 96% down to around 60% as the used catalyst was recycled. Addition of HCl helped to maintain the ethylene conversion so that the conversion stayed above 80% up to 65 hours on stream.

While we do not want to be bound by a theory, HCl or other source of Broensted acid appears to be required for ethylene alkylation. Initially ionic liquid catalysts contain a trace amount of HCl due to slight hydrolysis of the chloroaluminate catalyst during its synthesis. As the trace amount of HCl is consumed by side reaction(s), then the ethylene conversion starts to drop. Thus addition of HCl or a small addition of water to induce HCl formation would replenish the HCl needed to maintain the ethylene conversion.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A process for the production of high quality gasoline blending components comprising reacting a refinery stream containing an isopentane with a refinery stream containing an ethylene under alkylation conditions including an isopentane to olefin molar ratio of from 2 to 8 in the presence of a chloroaluminate ionic liquid catalyst comprising an alkyl substituted pyridinium chloroaluminate or an alkyl substituted imidazolium chloroaluminate of the general formulas A and B, respectively:

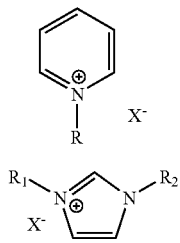

where R=H, methyl, ethyl, propyl, butyl, pentyl or hexyl group and X is a chloroaluminate, and R$_1$ and R$_2$=H, methyl, ethyl, propyl, butyl, pentyl or hexyl group and where R$_1$ and R$_2$ may or may not be the same; and wherein the isopentane and the ethylene are alkylated.

2. A process according to claim 1, wherein the ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

3. A process according to claim 1, wherein the catalyst further comprises an HCl co-catalyst.

4. A process according to claim 1, wherein the refinery stream containing an ethylene is derived by providing a first ethylene-containing refinery stream and separating a C$_{2+}$ fraction from said first stream to produce said refinery stream containing an ethylene, which is richer in ethylene than said first ethylene-containing refinery stream.

5. A process according to claim 1, wherein the refinery stream containing an ethylene comprises ethylene, propylene, butylenes and/or pentenes.

6. A process according to claim 1, wherein the alkylation conditions additionally include a catalyst volume in the reactor of from 5 vol % to 50 vol %, a temperature of from −10° C. to 100° C., a pressure of from 300 kPA to 2500 kPa, and a residence time of 1 minute to 1 hour.

7. A process according to claim 1, further comprising recovering high quality gasoline blending components of low volatility from said alkylation zone.

8. A process according to claim 7, further comprising blending said components into gasoline.

9. A process for the production of high quality gasoline blending components, comprising reacting a refinery stream containing an isobutane with a refinery stream containing an ethylene under alkylation conditions in the presence of a chloroaluminate ionic liquid catalyst comprising a hydrocarbyl substituted pyridinium chloroaluminate or an hydrocarbyl substituted imidazolium chloroaluminate of the general formulas A and B, respectively:

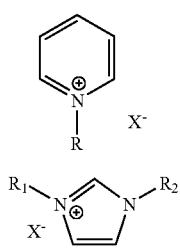

where R=H, methyl, ethyl, propyl, butyl, pentyl or hexyl group and X is a chloroaluminate, and R$_1$ and R$_2$=H, methyl, ethyl, propyl, butyl, pentyl or hexyl group and where R$_1$ and R$_2$ may or may not be the same; and wherein the isobutane and the ethylene are alkylated.

10. A process-according to claim 9, wherein the refinery stream containing an ethylene comprises ethylene, propylene, butylenes and/or pentenes.

11. A process according to claim 9, wherein the catalyst further comprises-an HCl co-catalyst.

12. A process according to claim 9, wherein the ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

13. A process-according to claim 9, wherein the refinery stream containing an ethylene is derived by providing a first ethylene-containing refinery stream and separating a C$_{2+}$ fraction from said first stream to produce said refinery stream containing an ethylene, which is richer in ethylene than said first ethylene-containing refinery stream.

14. A process according to claim 9, wherein the alkylation conditions include a catalyst volume in the reactor of from 5 vol % to 50 vol %, a temperature of from −10° C. to 100° C., a pressure of from 300 kPa to 2500 kPa, and a residence time of 1 minute to 1 hour.

15. A process according to claim 9, further comprising recovering high quality gasoline blending components of low volatility from said alkylation zone.

16. A process according to claim 15, further comprising blending said components into gasoline.

17. A process for the, production of high quality gasoline blending components comprising reacting a refinery stream containing an isobutane and isopentane with a refinery stream containing an ethylene under alkylation conditions in the presence of a chloroaluminate ionic liquid catalyst comprising a hydrocarbyl substituted pyridinium chloroaluminate or a hydrocarbyl substituted imidazolium chloroaluminate of the general formulas A and B, respectively:

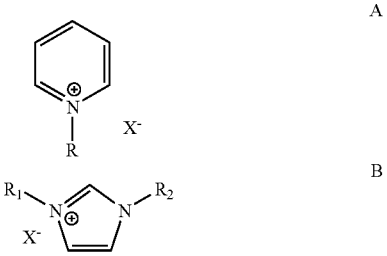

where R=H, methyl, ethyl, propyl, butyl, pentyl or hexyl group and X is a chloroaluminate, and R$_1$ and R$_2$=H, methyl, ethyl, propyl, butyl, pentyl or hexyl group and where R$_1$ and R$_2$ may or may not be the same; and wherein the isobutane and the isopentane and the ethylene are alkylated.

18. A process according to claim 17, wherein the refinery stream containing ethylene comprises ethylene, propylene, butylenes and/or pentenes.

19. A process according to claim 17, wherein the catalyst further comprises an HCl co-catalyst.

20. A process according to claim 17, wherein the ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

21. A process according to claim 17, wherein the refinery stream containing an ethylene is derived by providing a first ethylene-containing refinery stream and separating a $C_{2+}$ fraction from said first stream to produce said refinery stream containing an ethylene, which is richer in ethylene than said first ethylene-containing refinery stream.

22. A process according to claim 17, wherein the alkylation conditions include a catalyst volume in the reactor of from 5 vol % to 50 vol %, a temperature of from 10° C. to 100° C., a pressure of from 300 kPa to 2500 kPa, an isopentane to olefin molar ratio of from 4 to 8 and a residence time of 1 minute to 1 hour.

23. A process according to claim 17, further comprising recovering high quality gasoline blending components of low volatility from said alkylation zone.

24. A process according to claim 23, further comprising blending said components into gasoline.

25. A process for the production of high quality gasoline blending components comprising reacting a refinery stream containing an isoparaffin selected from the group consisting of isopentane, isobutane, and mixtures thereof, with a refinery stream containing an ethylene under alkylation conditions in the presence of a chloroaluminate ionic liquid catalyst comprising a hydrocarbyl substituted pyridinium chloroaluminate or a hydrocarbyl substituted imidazolium chloroaluminate of the general formulas A and B, respectively:

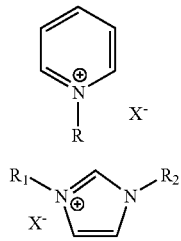

A

B where R=H, methyl, ethyl, propyl, butyl, pentyl or hexyl group and X is a chloroaluminate and $R_1$ and $R_2$=H, methyl, ethyl, propyl, butyl, pentyl or hexyl group and where $R_1$ and $R_2$ may or may not be the same; and wherein the isoparaffin and the ethylene are alkylated.

26. A process according to claim 25, wherein the refinery stream containing an ethylene comprises ethylene, propylene, butylenes and/or pentenes.

27. A process according to claim 25, wherein the catalyst further comprises an HCl co-catalyst.

28. A process according to claim 25, wherein the ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

29. A process according to claim 25, wherein the refinery stream containing an ethylene is derived by providing a first ethylene-containing refinery stream and separating a $C_{2+}$ fraction from said first stream to produce said refinery stream containing an ethylene, which is richer in ethylene than said first ethylene-containing refinery stream.

30. A process according to claim 25, wherein the alkylation conditions include a catalyst volume in the reactor of from 5 vol % to 50 vol %, a temperature of from −10° C. to 100° C., a pressure of from 300 kPa to 2500 kPa, and a residence time of 1 minute to 1 hour.

31. A process according to claim 25, further comprising recovering high quality gasoline blending components of low volatility from said alkylation zone.

32. A process according to claim 31, further comprising blending said components into gasoline.

33. The process of claim 17 or 25, wherein the alkylation conditions include an isopentane to olefin molar ratio of from 2 to 8.

34. The process of claim 1, 9, 17, or 25, wherein the chloroaluminate ionic liquid catalyst comprises a hydrocarbyl substituted pyridinium chloroaluminate of the general formula:

A

35. A process for the production of high quality gasoline blending components comprising reacting a refinery stream containing an isoparaffin selected from the group consisting of isopentane, isobutane, and mixtures thereof, with a refinery stream containing an ethylene underalkylation conditions in the presence of a chloroaluminate ionic liquid catalyst comprising a hydrocarbyl substituted pyridinium chloroaluminate of the general formula A:

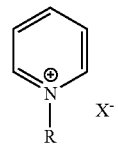

A where R=H, methyl, ethyl, propyl, butyl, pentyl or hexyl group and X is a chloroaluminate; and wherein the isoparaffin and the ethylene are alkylated.

36. The process of claim 35, wherein the alkylation conditions include an isopentane to olefin molar ratio, of from 2 to 8.

* * * * *